United States Patent
Odidi et al.

(10) Patent No.: US 6,800,668 B1
(45) Date of Patent: Oct. 5, 2004

(54) SYNTACTIC DEFORMABLE FOAM COMPOSITIONS AND METHODS FOR MAKING

(75) Inventors: Isa Odidi, Ontario (CA); Amina Odidi, Ontario (CA)

(73) Assignee: Intellipharmaceutics Corp., Mississauga (CA)

(*) Notice: Subject to any disclaimer, the term of this patent is extended or adjusted under 35 U.S.C. 154(b) by 66 days.

(21) Appl. No.: 09/765,783

(22) Filed: Jan. 19, 2001

(51) Int. Cl.$^7$ .................................................. C08J 9/04

(52) U.S. Cl. ...................... 521/134; 424/489; 521/84.1; 521/86; 521/88; 521/91; 521/92; 521/97; 521/138; 521/141; 521/149; 523/218; 523/219

(58) Field of Search ................................. 523/218, 219; 521/84.1, 86, 88, 91, 92, 97, 134, 138, 141, 149; 424/489

(56) References Cited

U.S. PATENT DOCUMENTS

| | | |
|---|---|---|
| 3,856,721 A | 12/1974 | Fritschel |
| 4,161,477 A | 7/1979 | Long et al. |
| 4,183,838 A | 1/1980 | Gagliani |
| 4,183,839 A | 1/1980 | Gagliani |
| 4,250,136 A | 2/1981 | Rex .......................... 254/257 |
| 4,425,441 A | 1/1984 | Gagliani et al. ............... 521/56 |
| 4,518,717 A | 5/1985 | Long et al. .............. 521/109.1 |
| 5,393,528 A | 2/1995 | Staab .......................... 424/436 |
| 5,795,583 A * | 8/1998 | Grune et al. ................. 424/400 |
| 6,090,401 A | 7/2000 | Gowan, Jr. et al. .......... 424/439 |
| 6,433,040 B1 * | 8/2002 | Dellamary et al. .......... 523/218 |

* cited by examiner

Primary Examiner—John M. Cooney, Jr.
(74) Attorney, Agent, or Firm—Licata & Tyrrell P.C.

(57) ABSTRACT

The invention relates to methods for preparing a syntactic foam composition suitable for use as a carrier for chemicals or other compounds, including pharmaceuticals. The invention further relates to compositions prepared in accordance with the methods of the present invention.

62 Claims, 9 Drawing Sheets

SYNTACTIC DEFORMABLE FOAM COMPOSITIONS AND METHODS FOR MAKING

FIELD OF TEE INVENTION

The present invention relates to methods of manufacturing foam compositions, for use in the preparation of pharmaceuticals or other chemical products. The invention further relates to syntactic foams which are deformable and/or compressible. The syntactic foam compositions of the present invention may be used as carriers, coated or uncoated for chemicals, biologicals, nutraceuticals, growth factors, amino acids, bioactive materials and pharmaceutically active and inactive materials and have pharmaceutical, sanitary, veterinary, agricultural and medical applications. The invention further relates to pharmaceutical and chemical syntactic foam compositions.

BACKGROUND OF THE INVENTION

Syntactic foam is material consisting of prefabricated, manufactured "bubbles" or microsphere fillers in a resin milieu. Syntactic foams having industrial applications are known.

Before the advent of syntactic foams, there were generally two types of foams: blown foams created by the injection of gas; and, self-expanding foams created through the use of chemicals. More recently, materials created by mixing a solid with minute spheres of glass, ceramic, or polymer are finding an increasing range of uses in industrial and high-tech applications.

Blown foams are made by, mixing or injecting a gas into a liquid and causing it to froth like soap bubbles in a bathtub. When the bubbles solidify a foam is created. Typically, self-expanding foams require the use of at least two chemical constituents: one to decompose into a gas to form the bubbles and one to form the walls of the cells. Again, when the bubbles solidify a foam is created.

On the other hand, syntactic foams use prefabricated or manufactured "bubbles" such as microspheres. Some refer to the microspheres as microballoons or even macroballoons. For the purposes of this application the term microspheres is used to include all of these terms and to also include spheres filled with air and spheres which are not filled with air, although it is generally recognized that spheres filled with air are preferred for the preparation of a syntactic foam. The microspheres are mechanically combined with a resin to form a composite material. In this way, the microspheres act as scaffoldings providing structure within the composite material which is formed. The term "syntactic" is derived from the Greek syntaktikos, meaning "to arrange together". Whereas blown and self-expanding foams develop a fairly random distribution of gas pockets of widely varying sizes and shapes, the porosity of syntactic foams can be much more closely controlled by careful selection and mixing of the microspheres with the resin milieu. Syntactic foams could also be called assembled foams.

While ordinary foams are visibly porous, syntactic foams can have cells so small that the material appears to be a homogeneous solid. Syntactic foams are typically used in deep-submergence vehicles, instrument packaging, electronic gear, cable buoys, floatation collars for deep-water drilling operations, radio frequency and aerospace applications, and by pattern-makers in factories. In other words, the foams are used in industrial applications where, for example, buoyancy is important.

The use of syntactic foams as carriers of coated or uncoated chemicals, biologicals, nutraceuticals, growth factors, amino acids, bioactive materials and pharmaceutically active materials for pharmaceutical, sanitary, veterinary, agricultural and medical applications is not common. Shortcomings in current methods of manufacture of syntactic foams thereby rendering them generally unsuitable for use as carriers particularly in the manufacture of pharmaceuticals include cost, difficulty of fabrication and assembly, high temperatures encountered during fabrication and toxicity of the materials used.

A review of the prior art shows that U.S. Pat. No. 3,856,721 discloses a syntactic foam produced by a controlled curing of a polymer which is a homopolymer of butadiene or a copolymer of butadiene and styrene or the like, at least 40% of which polymer is butadiene. Instead of styrene, a methyl or ethyl derivative may be used. The syntactic foam includes minute hollow spheres which give strength to the foam product and the syntactic foam product has a very low density. The polymeric material of this invention is subjected to a two-stage cure. The first stage being a low-temperature curing system utilizing methylethyl ketone (MEK) peroxide or other peroxides used in lower-temperature cures, cobalt naphthenate, iron naphthenate, and acetylacetone (pentanedione) or the like; the peroxide used in the second stage requiring a higher temperature for activation.

In U.S. Pat. No. 4,250,136, in the preferred form of the invention, a sandwich of composite materials is assembled and placed within a mold having the shape of the article to be formed. The composite sandwich is comprised of the following ingredients: (1) a first or bottom layer of reinforcing material such as fiberglass in woven or mat form; (2) a first layer of initially resilient and open-cell foam containing a liquid thermosetting resin such as epoxy, polyester, vinylester, or the like, is laid over the first reinforcing layer, (3) a second layer of reinforcing material is laid over the first resin-containing, open-cell foam layer; (4) a suitable quantity of uncured syntactic foam having a dough-like consistency is placed over the second reinforcing layer, (5) a third reinforcing layer is placed over the uncured and amorphous syntactic foam; (6) a second layer of liquid, resin-containing, open-cell, resilient foam is overlaid on the third reinforcing layer; and (7) a fourth or upper layer of reinforcing material is laid upon the second resin-containing foam layer. The composite sandwich is then placed within the mold and subjected to suitable heat and pressure to cause the uncured sandwich to assume the internal shape of the mold.

U.S. Pat. No. 4,425,441 discloses a high temperature and flame resistant closed cell polyimide foam material and methods of making the foam. An aromatic tetracarboxylic acid dianhydride is reacted with an oxontine to produce an N-substituted imide, which is then esterified with a suitable alcohol. The resulting liquid is dried and the dry residue is reduced to a uniform powder having particles with diameters generally in the 0.5 to 10 mm range. The powder is preferably further dried, either before or after final size reduction, in a moderate vacuum at moderate temperature to remove any excess residual alcohol. The powder spontaneously expands to form a closed cell foam when heated to a temperature in the range of about 90° to 150° C. for a suitable period. When the powder is expanded in a closed mold, a well consolidated, uniform, closed cell foam product results. When expanded in an unrestricted manner, closed cell "macroballoons" having average diameters between about 0.4 mm to 15 mm result.

U.S. Pat. No. 4,518,717 discloses methods of making low density modified polyimide/polyimide-amide foams and the resulting compositions. An N-substituted aliphatic imide is prepared by reacting a suitable aromatic dianhydride with a suitable oxime. A polyimide forming material is prepared by dissolving the N-substituted aliphatic imide in an esterifying solvent, then adding a suitable aromatic diamine. This material is dried to a powder. A suitable hydrated compound which is stable up to at least about 100° C. is mixed with the powder. A foam is then produced by heating the material to reaction temperature for a period sufficient to produce a stable foam. The material melts, then spontaneously expands into a foam which becomes self supporting and cures to a resilient flexible foam. The addition of the hydrated compound is found to result in an exceptionally low density foam. Depending upon heating conditions, a polyimide, polyimide-amide or mixture thereof may be produced, resulting in foams having selectively variable physical properties.

Prior U.S. Pat. Nos. 4,161,477, 4,183,838 and 4,183,839 disclosed and claimed certain polyimide compositions which are flame resistant and useful as coatings and adhesives. The coating and adhesive compositions described in the above-mentioned prior patents are made by first preparing a suitable bisimide by reacting an aromatic tetracarboxylic acid dianhydride with a cyclic amide or oxime. The imidization reaction is preferably conducted at a temperature of 170°–200° C. for 20–60 minutes. The polyimide forming material is then prepared by dissolving the bisimide in an inert solvent; then adding thereto a suitable diamine, producing a viscous fluid containing an intimate, unpolymerized mixture of N-substituted cyclic bisimide dicarboxylic acid and diamine which is capable of being converted to a high molecular weight polymer by the application of heal The solution is coated onto a surface and polymerized by heating to a temperature in the 177°–316° C. range for 30 minutes to 5 hours.

A foamed ibuprofen-containing dosage is disclosed in German patent application 19635676. A mixed copolymer of N-vinylpyrrolidone and vinyl acetate is melted with ibuprofen. The melt is impregnated with carbon dioxide gas while being passed through an extruder. The carbon dioxide expands to yield bubbles impregnated in the melt after it exits from the extruder. This is not a syntactic foam.

According to U.S. Pat No. 5,393,528, a foam for the vaginal delivery of active materials can be prepared by mixing HPMC, glycerin, and the active ingredient, and introducing nitrogen gas while mixing to form a frothy foam. The mixture is then cast as a foamed film on a solid surface. This is not a syntactic foam.

U.S. Pat. No. 6,090,401 discloses methods of preparing an edible comestible suitable for human consumption, comprising either providing a polymeric foaming agent; optionally a non-cellulosic polysaccharide, a solvent and a therapeutically effective dose of a pharmaceutically active ingredient; admixing said polymeric foaming agent, non-cellulosic polysaccharide, solvent and pharmaceutically active ingredient; forming a foam dispersion from the admixed mixture; or a method of preparing an edible comestible suitable for human consumption, comprising dissolving a foaming agent in a solvent to yield a solution of said foaming agent, dispersing bubbles of gas in the foaming agent solution to yield a foam dispersion, drying said foam dispersion such that the dried foam dispersion has a bulk density of less than about 0.4 grams/cubic centimeter. In both cases an entrained gas is used.

It would be advantageous if suitable syntactic foams could be prepared for use as powders other suitable carriers for pharmaceutical actives and other chemical compounds. The syntactic foams found in the prior art are generally unsuitable for these purposes because of manufacturing complexities thereby increasing the costs of manufacture, the use of reagents which are not suitable for human or animal consumption, the creation of byproducts not suitable for human or animal consumption and/or the requirement for high temperatures which are likely to inactivate the activity of the pharmaceutical active or other biologicals.

A further advantage of the present invention is the ability of the syntactic foam preparations of the present invention to permit time release of pharmaceuticals in a mammal, particularly humans. It is foreseen that the preparations of the present invention could be used to reduce the frequency that a particular medicine needs to be taken. For example, certain medications presently require three or times per day dosages and the present invention may be useful in reducing the number of daily doses to two or one.

SUMMARY OF THE INVENTION

In accordance with an aspect of the present invention there is provided a syntactic foam composition that looks and behaves like a homogeneous solid. In accordance with another aspect of the present invention there is provided a syntactic foam composition suitable for use as a carrier for the delivery of one or more pharmaceuticals or other chemical. In accordance with another aspect of the present invention, there are provided methods of manufacturing these syntactic foam compositions. In accordance with a further aspect of the invention, these methods are economical and versatile manufacturing processes.

In accordance with another aspect of the present invention, there is provided syntactic pharmaceutical foam compositions which are carriers, coated or uncoated, which contain chemicals biologicals, nutraceuticals, growth factors, amino acids, bioactive materials, pharmaceutically active materials and pharmaceutically inactive materials. These compositions may be used for pharmaceutical, sanitary, veterinary, agricultural and medical applications, for example. In accordance with an aspect of the present invention, such pharmaceutical or chemical syntactic foam compositions are manufactured in accordance with the methods of the present invention.

In accordance with yet another aspect of the present invention, there is provided safe, stable, syntactic foam compositions in combination with one or more pharmaceutical actives or preparations for delivery to humans and other mammals as pharmaceutical preparations.

In accordance with an aspect of the present invention, there is provided a method of preparing a deformable syntactic foam for the delivery of a compound or chemical, the method comprising:

a) mixing together one or more homopolymer resins, one or more binders, and one or more stabilizers to form a blended mixture having a LOD of from about 1% to about 10%; and b) reacting the blended mixture with one or more organic solvents under conditions of high shear at temperatures of from about 10° C. to about 25° C. until a foam composition is formed wherein the foam composition is deformable to the touch. A method of manufacturing a pharmaceutical carrier, the method comprising the steps of:

a) mixing together:
 i) one or more pharmaceutically acceptable homopolymer resins;

ii) one or more pharmaceutically acceptable binders;
iii) pharmaceutically acceptable microspheres, or other suitable scaffolding element, and
iv) one or more pharmaceutically acceptable stabilizers to form a blended mixture having an LOD of from about 1% to about 10%;
b) reacting the blended mixture with one or more pharmaceutically acceptable organic solvents under conditions of high shear at temperatures of from about 10° C. to about 25° C. until a foam composition is formed wherein the foam composition is deformable to the touch; and
c) reducing the size of the deformable syntactic foam to permit reassembly into a shaped composite.

In accordance with another aspect of the present invention, the mixture in step (a) further comprises a particulate substance which can act as a scaffolding. By the term scaffolding what is intended is that the particulate substance provide a certain regularity and/or strength to the resultant foam composition.

In accordance with another aspect of the present invention, the particulate substance is substantially spherical. Under the conditions of the present invention, the substantially spherical particles align themselves with a certain regularity or ordered arrangement of linear arrays. Advantageously, substantially spherical particles have the added benefit that they may be created to contain a medication or provide a point of binding, covalent or otherwise, for a compound, molecule or medicine which is to be distributed within the composition for subsequent delivery to a system or to a living organism.

In a particularly preferred embodiment the substantially spherical substance comprises substantially spherical microparticles such as microspheres. Microballoons is another term used in the art. There is little distinction to be made between these two terms other than the possible connotation that microballoons have a substantial air space within them whereas a microsphere may not, and also others skilled in the art may consider microballoons to be of a slightly larger size than microspheres. In the present application the term microsphere is used to include all substantially spherical microparticles such as microballoons, macroballoons or other similar elements and/or terminology as used in the art.

The regularity of spherical particles such as microspheres or microballoons is such that under the method steps of the present invention the substantially spherical particles tend to align and form groupings with regularly spaced interstices between the microparticles. When the foam composition as prepared by the method of the present invention is used as a carrier for a compound, molecule or medicine, the interstices may trap the compound, molecule or medicine. The entrapment of the medicine either distinct from, or in addition to, may be used to facilitate time release of the compound, molecule or medicine from the composition preparation.

In a preferred embodiment of the present invention, the particles have a diameter of about 1000 micrometers, or less. In a particularly preferred embodiment the particles are microspheres having a diameter of about 1000 micrometers, or less.

In accordance with another aspect of the present invention, the loss on drying (LOD) is checked intermittently during the mixing under high shear. In accordance with a preferred embodiment of the present invention, when the LOD of the reacted mixture is from about 2 percent to about 25 percent the mixing under high shear conditions is stopped. It is in this LOD range that a preferred foam composition is made by the methods of the present invention.

In accordance with another aspect of the present invention, the foam composition as prepared by the methods of the present invention may be milled or otherwise broken down into smaller particle sizes. If microspheres or other substantially spherical particles are present in the composition it may have a stringy or dendritic look to the particles as they are separated. This reflects the tendency of the microspheres to form arrays during the method steps of the present invention.

A compound, chemical or medicine may be added to the microspheres or as part of the blended mixture before high shear treatment. Alternatively, after the method of the present inventions are complete and a syntactic deformable composition has been created, a compound, chemical or medicine may be added at the end with or without breaking down the foam. The compound, chemical or medicine could be bound to the scaffolding elements, e.g. microspheres, or it could be retained for a shorter period of time in the interstices of between the microspheres. The interstices are the spaces formed by abutting microspheres.

In accordance with another aspect of the present invention. The syntactic foam composition of the present invention may be shaped into a shaped composite after the foam is created. A variety of shapes may be used depending on the ultimate usage of the product. The composition may also be used in other preparations as well.

In accordance with an aspect of the present invention, the preferred stabilizer is silicic anhydride.

In accordance with an aspect of the present invention, the preferred organic solvent is 2-propanol.

In accordance with an aspect of the present invention, the preferred homopolymer resin is a carboxyvinyl polymer.

In accordance with an aspect of the present invention, the preferred the microspheres are selected from the group consisting of silica, sucrose, glucose, lactose, dextrose, sorbitol, mannitol, xylitol, dextrates, poly(lactic acid), poly(glycolic acid), poly(glycolic acid-co-lactic acid), poly($\epsilon$-caprolactone), poly(malic acid), cellulose, microcrystalline cellulose, metal, glass and small beads.

In accordance with an aspect of the present invention, the preferred method according to any one of the above claims wherein the blended mixture further comprises a binder as part of the blended mixture.

In accordance with an aspect of the present invention, the preferred binder is selected from the group consisting of high molecular weight polysaccharide, xanthan gum, d-$\alpha$-tocopherol polyethylene glycol 1000 succinate, starch NF, povidone, copolyvidone NF, polyvinyl alcohols, glyceryl behenate, xanthan gum, polyethelene glycols, polyethelene oxides, cellulose binders, hydroxypropyl Methylcellulose USP and hydroxyethyl Cellulose NF.

In accordance with an aspect of the present invention, the preferred binder is a high molecular weight polysaccharide, more preferably a Xanthan gum and yet more preferably a d-$\alpha$- tocopherol polyethylene glycol 1000 succinate.

In accordance with another aspect of the present invention, the deformable syntactic foam prepared by the methods of the present invention is reduced in size by drying (LOD less than about 5%) and then milling before shaping into a composite for use as a carrier or use in a chemical or pharmaceutical composition.

In accordance with another aspect of the present invention, there is provided a composition comprising a chemical, compound or medicine such as a pharmaceutical together with a carrier made by the methods of the present invention.

In accordance with another aspect of the present invention there is provided a composition comprising a chemical, compound or medicine together with a syntactic foam prepared in accordance with the methods of the present invention.

In accordance with a preferred embodiment of the present invention, there is provided a composition comprising a pharmaceutical is selected from the group consisting of human and veterinary medicines and a syntactic foam prepared in accordance with the methods of the present invention.

In accordance with another aspect of the present invention, the compositions of the present invention further comprise the preparation step of applying a coating agent to the foam before a size reduction step or after a shaped composite is prepared.

In accordance with another aspect of the present invention, the pharmaceutical compositions of the present invention are suitable for use in time release or controlled release preparations.

In accordance with another aspect of the present invention, the pharmaceutical used in the compositions of the present invention is either an active or else an inactive metabolite of an active pharmaceutical ingredients or salts of the metabolites of active pharmaceutical ingredients.

In accordance with another aspect of the present invention, the compositions of the present invention comprise a pro-drug which after oral administration generates active or inactive metabolites.

In accordance with another aspect of the present invention, the compositions of the present invention comprise a precursor chemical or compound which after oral administration to an animal or a human generates either pharmaceutically active or inactive metabolites.

In accordance with another aspect of the present invention, the pharmaceutical compositions of the present invention further comprise according to any one of become systemically available over a period of not less than two hours after administration to a human or other mammal.

In accordance with another aspect of the present invention, the pharmaceutical compositions of the present invention are time-released or controlled release preparations.

In accordance with another aspect of the present invention, the compositions of the present invention, elicit pharmacological or therapeutic activity.

Other and further advantages and features of the invention will be apparent to those skilled in the art from the following detailed description thereof taken in conjunction with the accompanying drawings.

DETAILED DESCRIPTION OF THE PREFERRED EMBODIMENTS

The present invention relates to methods for preparing syntactic foam compositions. In certain preferred compositions scaffolding elements are used in the compositions and in particularly preferred embodiments the scaffolding element is microspheres. In the present application the term microsphere is used to include all substantially spherical microparticles such as microballoons, macroballoons or other similar elements. The invention further relates to syntactic foam compositions prepared in accordance with these methods.

The basic steps in producing the syntactic foams of the present invention comprise blending one or more homopolymer resins; one or more binders; microspheres; and one or more stabilizers. Then, reacting the blended mixture with one or more organic solvents under high shear forces at temperatures between about 10° C. and about 25° C. to form a syntactic, deformable and/or compressible pharmaceutical foam. The resultant preparation will have long thread-like portions which are dendritic in nature.

If the syntactic foam is intended for use as a pharmaceutical carrier or for use in the formulation of a medicine, it is necessary to select the components of the foam so as to be pharmaceutically acceptable. For example, pharmaceutically acceptable homopolymer resins, binders, microspheres, stabilizers and organic solvents would be used in the manufacture of a syntactic foam preferred for use as a carrier in a pharmaceutical composition. In a particularly preferred embodiment, the microspheres are cellulose, the organic solvent is 2-propanol, the homopolymer resin is a carboxyvinyl polymer, a high molecular weight polysaccharide as the binder and the stabilizer is silicic anhydride.

The shape and speed of the device generating the high shear forces together with the combination and ratios of the materials and mixing times utilized are chosen so as to obtain a physico-chemically stable syntactic deformable and compressible dendritic foam with a loss on drying of 8% to 20%.

The length of time for the blended mixture to change from a free flowing powdery state to syntactic, deformable or compressible, dendritic foam composition will vary depending on the size of the batch, the amount of solvent, and the speed of mixing in a high shear mixer. A person skilled in the art would know when the deformable composition has been achieved. Intermittently the blending is stopped to see if it is deformable. There is a disadvantage to overblending. The mixture is blended only until the resulting blended mixture is deformable to the tough meaning that it holds together as if it was a homogeneous solid but upon pressure it can be deformed. If blended too much the mixture will become rubbery. One skilled in the art will be able to ascertain when there is sufficient mixing but not too much by intermittently checking the mixture to see if it is gently deformable to the touch. Batches of similar sizes and composition will take the same length of time from batch to batch at approximately the same speed of high shear mixing.

The syntactic deformable and compressible dendritic foam can be disentangled into discrete particles of any size or it can be cut into particles of any size. In preferred embodiments the foam is disentangled into particles of less than about 1000 µm in diameter. In one embodiment, the syntactic foam created by the present invention is treated first with a cryogenic fluid, or by lyophylization freeze drying, or by drying at between 25 degrees centigrade and 60 degrees centigrade, before any size reduction step.

Pharmaceutically acceptable homopolymer resins suitable for use in the present invention, and include homopolymers of acrylic acid crosslinked with allyl sucrose or allyl pentaeydiritol, homopolymers of acrylic acid crosslinked with divinyl glycol, homopolymers of acrylic acid with long chain alkyl acrylate comonomers crosslinked with allyl pentaerydiritol having molecular weight of 500,000 to 10 billion. Particularly suitable, for example, are the crosslinked polyacrylic acids available from the B.F. Goodrich Co. under the trade name Carbopol® and Noveon® resins. Especially preferred are Noveon® AA-1 USP, Carbopol® 971P NF, Carbopol® 934P NF, and Carbopol® 974P NF.

Examples of suitable binders useful in the present invention include the binder is selected from the group consisting of high molecular weight polysaccharide, xanthan gum, d-α-tocopherol polyethylene glycol 1000 succinate, starch NF, povidone, copolyvidone NF, polyvinyl alcohols, glyceryl behenate, xanthan gum, polyethylene glycols, polyethylene oxides, cellulose binders, hydroxypropyl Methylcellulose USP and hydroxyethyl Cellulose NF and particularly preferred are hydroxypropyl Methylcellulose USP and hydroxyethyl Cellulose NF.

In a preferred embodiment, the compositions of the present invention also include scaffolding or filler elements. In a preferred embodiment the scaffolding is microspheres and this term is intended to include all particles of suitable size whether perfectly spherical or not and, in particular, this term includes microballoons and macroballoons as described elsewhere in the art. Although microspheres are the preferred "scaffolding" or "filler" element it is possible that a syntactic foam could be created in the absence of microspheres. In this instance it would likely be necessary to include additional polymer and/or binder in the composition to compensate for the missing microspheres.

Figure 1:
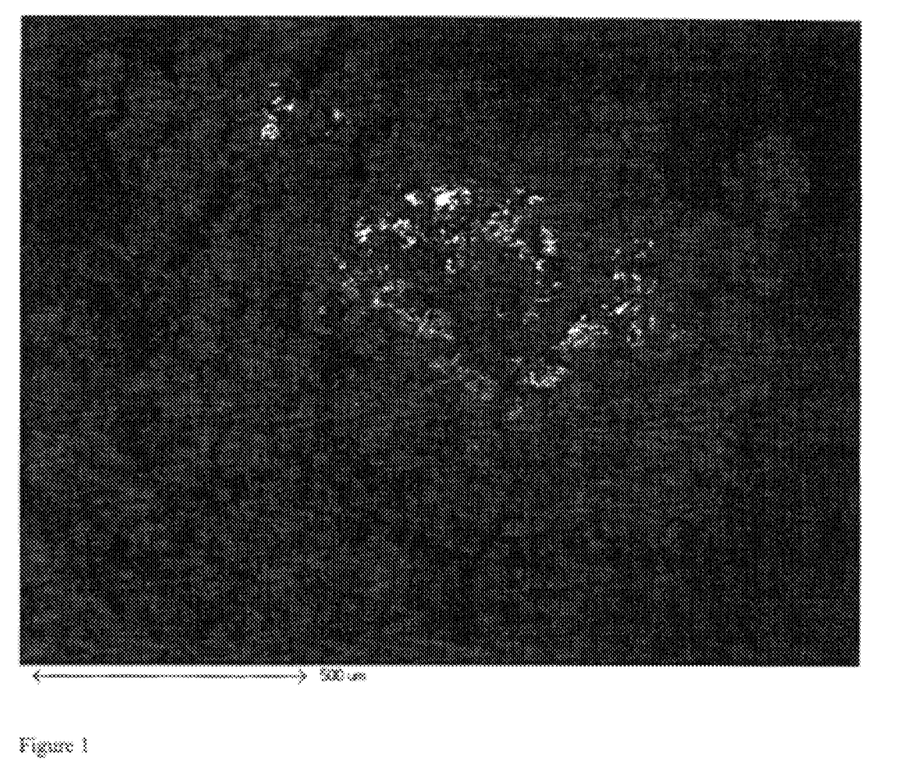
FIG. 1 is a scanning electron micrograph of a syntactic foam prepared in accordance with a method of the present invention showing microspheres as scaffolding in a homopolymer resin.
Figure 2:
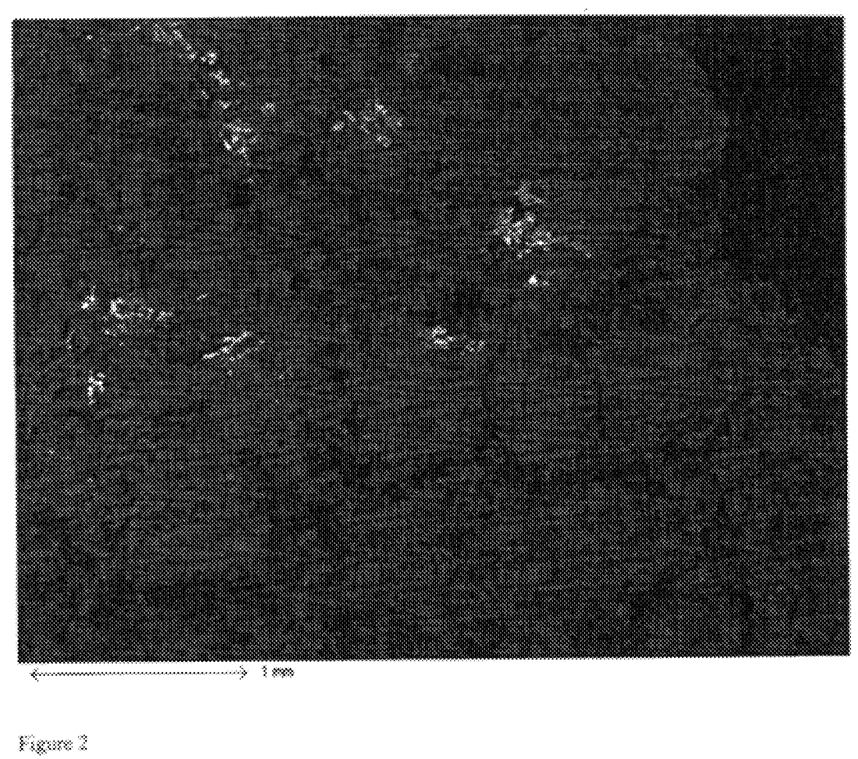
FIG. 2 is a scanning electron micrograph of a syntactic foam prepared in accordance with a method of the present invention showing arrays of microspheres acting as scaffolding in the preparation.
Figure 3:
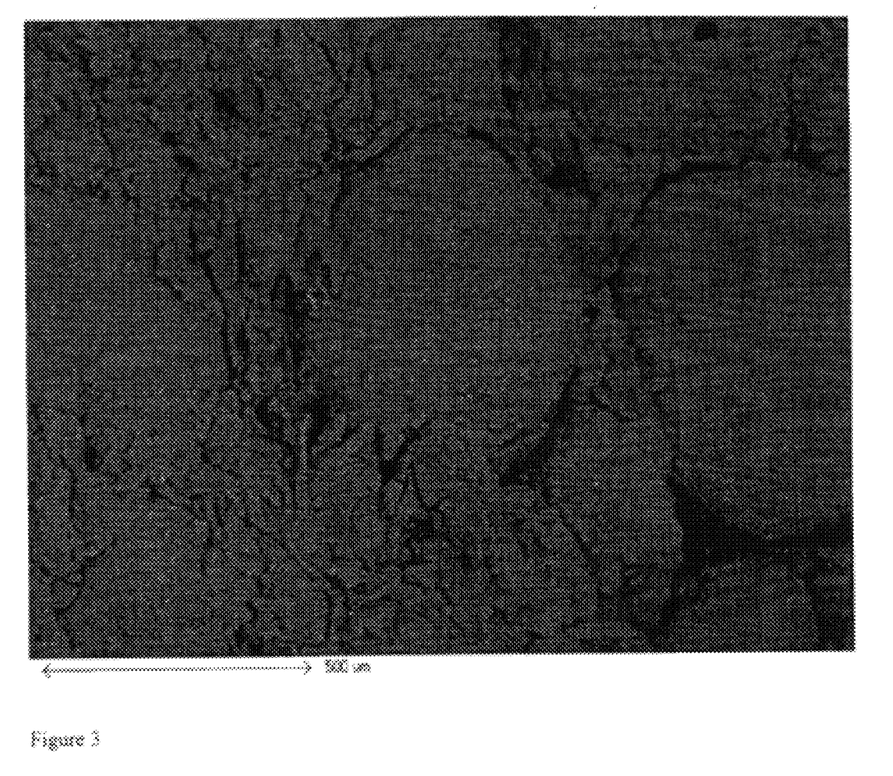
FIG. 3 is a scanning electron micrograph of a syntactic foam prepared in accordance with a method of the present invention illustrating the arrays of the microspheres acting as scaffolding in the preparation and also the interstices between the microspheres.
Figure 5:
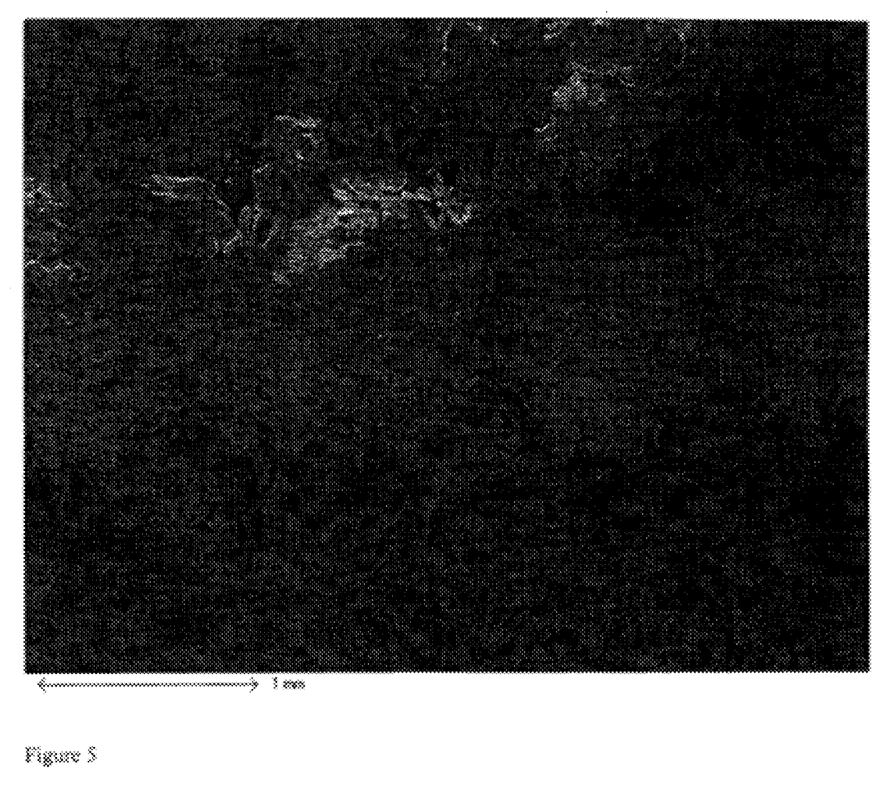
FIG. 5 is a scanning electron micrograph illustrating the attachment and/or presence of binders in the syntactic foam preparation and around the surfaces of the microspheres.

FIGS. 1, 2, and 3 are scanning electron micrographs illustrating the microspheres as they appear in a syntactic foam composition prepared in accordance with the methods of the present invention. Binders can be seen in these figures as well as in FIGS. 5, 6 and 7, for example.

In a most preferred embodiment the microspheres are less than 1000 µm in diameter. Examples of pharmaceutically acceptable microspheres include microspheres made of silica, sucrose, glucose, lactose, dextrose, sorbitol, mannitol, xylitol, dextrates, poly(lactic acid), poly(glycolic acid), poly (glycolic acid-co-lactic acid), poly(c-caprolactone), and poly(malic acid). Particularly suitable microspheres are those made of cellulose or microcrystalline cellulose. While cellulose is a preferred embodiment for the microspheres of the present invention, even metal or glass microspheres or small beads could work to create the syntactic foam. Although such substances would generally not be approved for human consumption as a pharmaceutical product, they may be suited to other applications.

It is noted that microspheres which are not filled with air should also work in the present invention.

The scaffolding provided by the particles, such as microspheres, may be regularly shaped or irregularly shaped. Irregularly shaped particles of scaffolding may be added to increase the physical strength of the syntactic foam in tension and/or compression.

The organic solvent used in the methodology of the present invention, is used to react together the dry and free flowing admixture of resin, binder, scaffolding and stabilizer. Especially preferred is 2-propanol as solvent. It is expected that ethylacetate may also work. Aqueous solvents may also be useful to the extent that they could be combined with an organic solvent for use as a solvent mixture. Typically the solvent is added after the other ingredients have been mixed so that it acts upon the mixture as a whole to cause the necessary chemical reaction towards forming a syntactic foam.

The rate of high shear agitation, the amount of solvent and the length of time for which the admixture is reacted with the solvent under high shear is carefullly controlled during the application of the high shear forces to the mixture so as to result in a stable syntactic deformable and compressible dendritic solid foam. Samples are taken intermittently to determine the moisture loss during the process and to assess the deformability of the composition. A Loss on Drying (LOD) of 8% to 20% is particularly preferred.

The foam produced by the methodology of the present invention is sufficiently stable so that it can be cut into uniform sections even before drying.

The syntactic foam prepared in accordance with the methods of the present invention can be used for the delivery of chemicals, compounds, molecules, and other preparations, including medicines.

The syntactic foam of the present invention contains microspheres which serve to provide a scaffolding or structure to the syntactic foam made by the methods of the present invention. When the syntactic foam is made by the present methods, the microspheres create a regularity to the structure of the foam. The regularity is seen in the final product as dendritic, string-like structures which show the microspheres forming regular arrays. In the spaces, also referred to as interstices or joints, formed where the microspheres or other suitable substantially spherical particle abut, certain chemicals, compounds, molecules or pharmaceuticals could reside either loosely or by covalent or non-covalent binding to the particles or microspheres. In the case where the microspheres are hollow, such chemical, compound, molecule or medicine could also be contained within the microsphere directly.

The location of a compound in the interstices or in the microspheres themselves could impact the release and/or rate of release of the compound into a surrounding environment.

FIGS. 4 to 7 illustrate the interstices between microspheres at varying magnifications.

The microspheres can either be purchased from a commercial provider or they can be made from scratch. If the syntactic foam is not intended for ingestion then the microspheres can be made of a wide variety of materials, including glass. However, if the syntactic foam of the present invention is to be used for pharmaceutical applications then microspheres made of sugars, cellulose or other substance which is approved for human consumption would be necessary in order to make a pharmaceutically acceptable syntactic foam composition.

The microspheres serve not only as structural scaffolding for the syntactic foam but also as structure for the incorporation of a medicine, chemical or other compound or molecule, into the foam itself. The medicine, chemical, compound or molecule may be incorporated inside microspheres or bound, either covalently or noncovalently, to the surface of the microspheres.

The incorporation of a medicine, chemical, compound or molecule either into or onto the microspheres can be done wither before or after the syntactic foam is made. For Example, a medicine or chemical could be incorporated inside the microspheres if the microspheres are made from scratch. These pharmaceutically enhanced microspheres could then be used in the mixture when preparing the syntactic foam. The resulting syntactic foam would therefore be a pharmaceutical syntactic foam composition and it would be ready for farther processing and/or molding into a suitable form such as a tablet or caplet. Before or after shaping, one or more pharmaceutically acceptable coatings could be applied to the pharmaceutical syntactic foam composition.

In another example, the pharmaceutical could be incorporated into, onto or between the microspheres after the syntactic foam has been made. The microspheres will form spaces or gaps between themselves in which a pharmaceutical active or other medicine could be trapped. After the pharmaceutical active or other medicine is added to the syntactic foam a pharmaceutical syntactic foam composition is created and is ready for further processing and/or molding.

Once the syntactic deformable foam is created it can either be used as a solid block or it can be further processed to reduce the apparently homogeneous solid into particles. The size of the particles will vary depending on the caliber of sieve or the degree of grinding and or milling which is applied. The microspheres create a dendritic nature to the foam and the dendritic strings of microspheres can be separated into various particle sizes by disentangling and breaking them down.

In order to break down the foam it may be advantageous to treat it by lyophylization or freeze drying before separation into particles. The particles can then be further separated into specific sizes by milling and/or sieving. The preferred particle size is about 1000 μm, or less.

In other instances it may be advantageous to treat the syntactic deformable foam to make it more rigid before breaking down and separating out particles. One way to do this is to contact the syntactic foam product with a cryogenic fluid. Preferred cryogenic fluids include liquid nitrogen and liquid carbon dioxide. After treatment then the resultant frozen product would be ground into smaller particle sizes and separated to achieve a preferred particle size of about 1000 μm or less.

Figure 8:
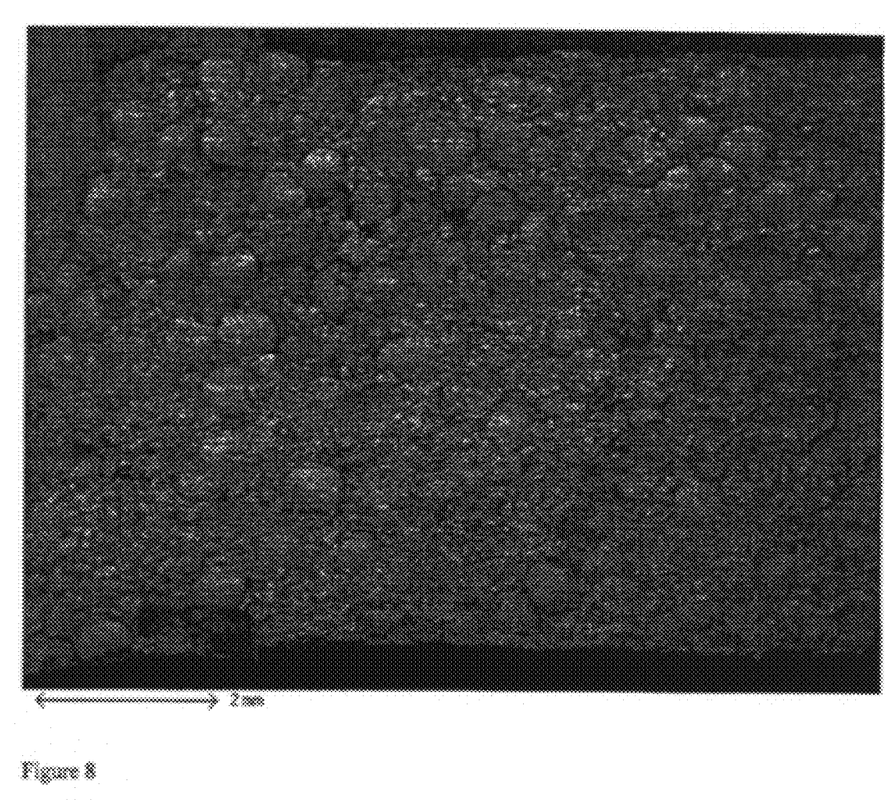
FIG. 8 is a scanning electron micrograph illustrating a syntactic foam prepared in accordance with a method of the present invention after the foam was dried, size reduced to discrete particles and reassembled under compression forces into a composite.
Figure 9:
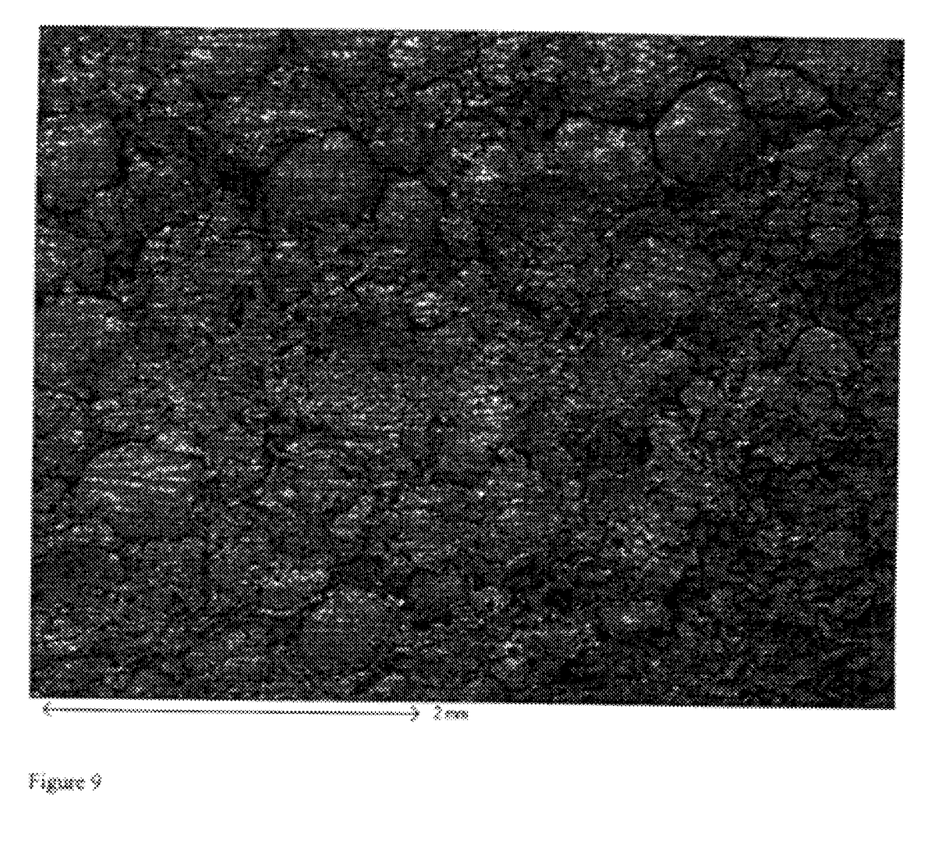
FIG. 9 is a scanning electron micrograph illustrating a syntactic foam prepared in accordance with a method of the present invention after the foam was dried, size reduced to discrete particles and reassembled under compression forces into a composite.

Once the particles are created then they can be treated flirter and processed further to prepare a pharmaceutical or chemical preparation and/or then molded into a shape. In the case of a pharmaceutical a preferred shape would be a tablet or a caplet. This processing could occur by way of a compression step forming the foam, either before or after disentangling or reduction to particles, into a shaped composite. FIGS. 8 and 9 illustrate a syntactic foam prepared in accordance with the methods of the present invention after drying and size reduction and reassembly into a composite by compression forces. In these figures it is to be observed also that the microspheres remain substantially intact even after these steps of size reduction and compression. The particles created during size reduction could be large or small depending their intended purpose.

In the case of pharmaceuticals the pharmaceutical could be selected from the group consisting of human and veterinary medicines.

Specifically the pharmaceutical or pharmaceutical active could be selected from the group of pharmaceuticals having one or more active ingredients selected from the group consisting of Acarbose, Acetaminophen/Codeine, Albuterol, Alendronate, Allopurinol, Alprazolam, Amitriptyline, Amlodipine, Amlodipine/Benazepril, Amoxicillin, Amoxicillin/Clavulanate, Amphetamine Mixed Salts, Aspirin, Atenolol, Atorvastatin, Azithromycin, Beclomethasone, Benazepril, Bisoprolol/HCTZ, Brimonidine, Carbidopa-Levodopa, Calcitonin, Carisoprodol, Carvedilol, Cefprozil, Cefuiroxime, Celecoxib, Cephalexin, Cetrizine, Ciprofloxacin, Cisapride, Citalopram, Clarithromycin, Clonazepam, Clonidine, Clopidogrel, Clotrimazole/Betamethasone, Cyclobenzaprine, Diazepam, Misoprostol, Digoxin, Divalproex, Donepezil, Doxazosin, Enalapril, Erythromycin, Estradiol, Ethinyl Estradiol/Norethindrone, Famotidine, Felodipine, Fexofenadine, Fexofenadine/Pseudoephedrine, Fluoxetine, Fluticasone Propionate, Fluvastatin, Fluvoxamine, Fosinopril, Furosemide, Gemfibrozil, Glimepinide, Glyburide, Granisetron, Guaifenesin/Phenylpropanolamine, Hydrochlorothiazide, Hydrocodone w/APAP, Ibuprofen, Ipratropium, Ipratropium/Albuterol, Irbesartan, Isosorbide Mononitrate, Lansoprazole, Latanoprost, Levofloxacin, Levonorgestrel/Ethinyl Estraliol, Levothyroxine, Lisinopril, Lisinopril/HCTZ, Loratadine, Loratidine/Pseudoephedrine, Lorazepaam, Losartan, Losartan/HCTZ, Lovastatin, Mateglinide, Mesalamine, Methylprednisolone, Metoprolol, Miglitol, Mometasone, Montelukast, Morphine, Mupirocin, Naproxen, Nisoldipine, Nitrofiurantoin, Nizatidine, Ofloxacin, Olanzapine, Ondansetron, Oxaprozin, Oxycodone, Oxycodone/APAP, Paroxetine, Penicillin VK, d-phenylalanine amino acid derivatives, Phenytoin, Potassium Chloride, Pramipexole, Pravastatin, Piednisone, Promethazine, Propoxyphene N/APAP, Propranolol, Quetiapine, Quinapril, Raloxifene, Ramipril, Ranitidine, Repaglinidc, Risperidone, Rofecoxib, Salmeterol, Sertraline, Sildenafil, Simvastatin, Sotalol, Sumatriptan, Tamoxifen, Tamsulosin, Temazepam, Terazosin, Terbinafine, Tobramycin/Dexamethasone, Tolterodine, Tranylcyprotine, Trazodone, Triamterene/HCTZ, Troglitazone, Valsartan, Venlafaxine, Warfarin, Zafirlukast, and Zolpidem.

In other examples, the composition could comprise a pharmaceutical active selected from the group consisting of abacavir, amprenavir, staviudine, zalcitabine, didanosine, delavivdine, efavirenz, hydroxyurea, indinavir, lamivudine, lopinavir, nelfinavir, nevirapine, ritonavir, saquinavir and zidovudine.

In another example, the composition comprises a pharmaceutical active which is a cyclooxygenase inhibitor such as COX-1 or COX-2. In another example the COX-2 inhibitor could be either celecoxib or rofecoxib.

The pharmaceutical or pharmaceutical active could be retained in the interstices between the microspheres, non-covalently bound to the microspheres, covalently bound to the microspheres or contained within the microspheres.

Figure 4:
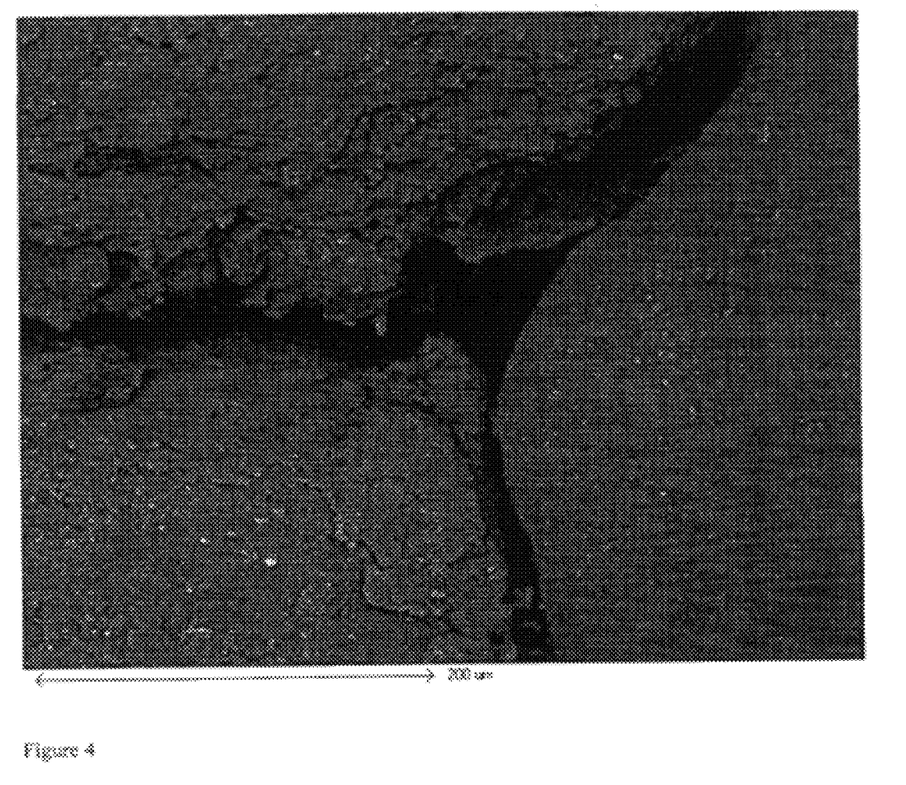
FIG. 4 is a scanning electron micrograph of a syntactic foam prepared in accordance with a method of the present invention illustrating in greater magnification an interstice between three abutting microspheres.
Figure 6:
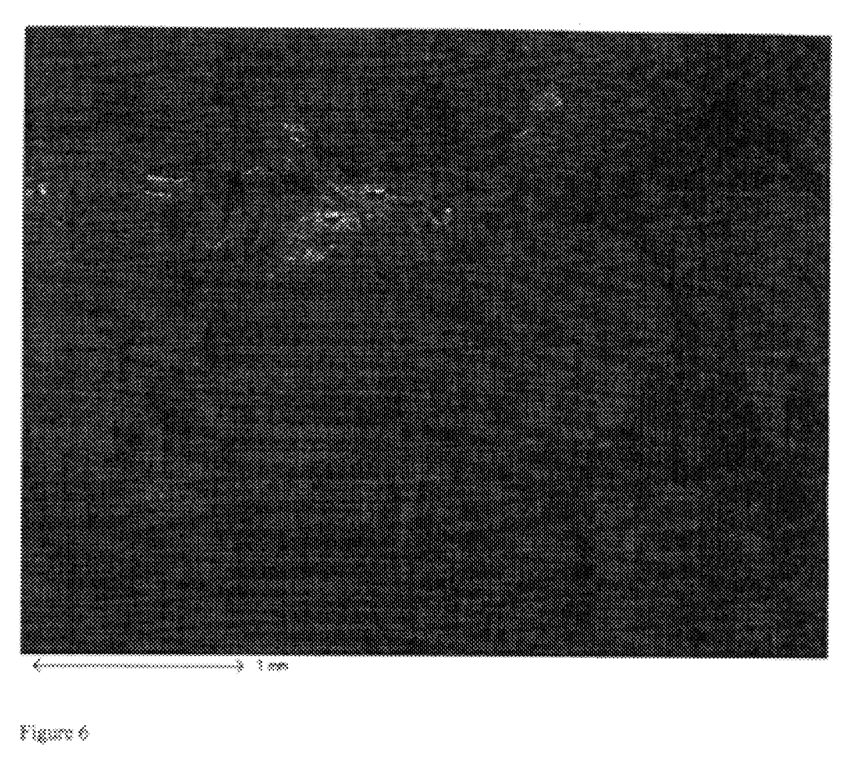
FIG. 6 is a scanning electron micrograph illustrating the attachment and/or presence of binders in the syntactic foam preparation and around the surfaces of the microspheres.
Figure 7:
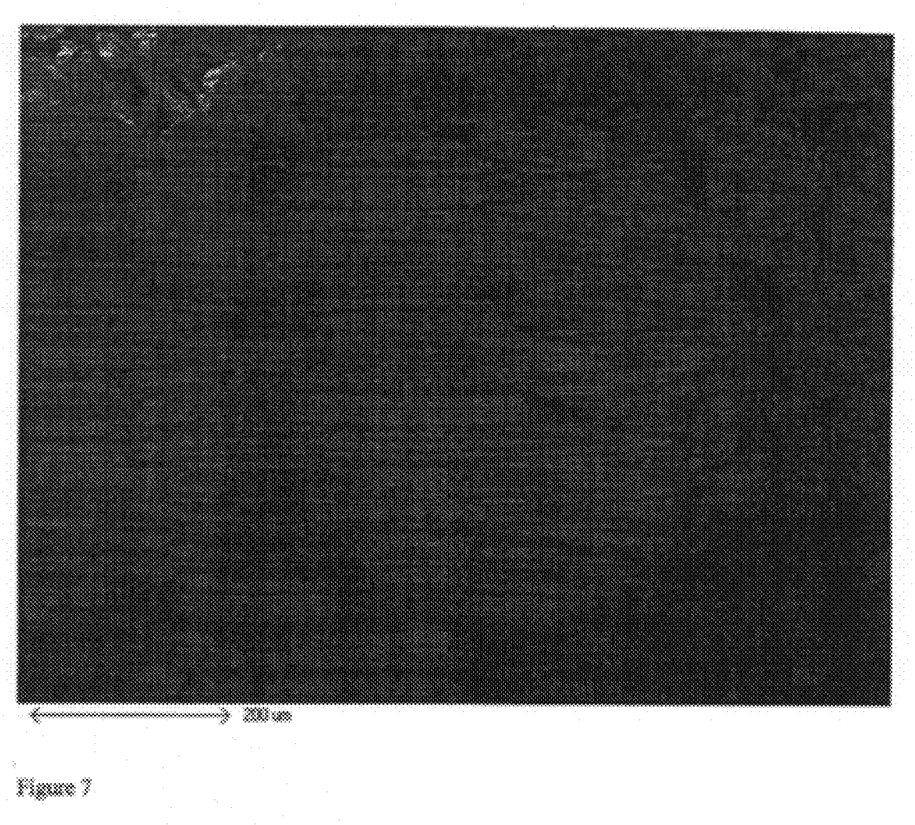
FIG. 7 is a greater magnification scanning electron micrograph illustrating the attachment and/or presence of binders in the syntactic foam preparation and around the surfaces of the microspheres.

FIGS. 4, 6 and 7, for example, illustrate by way of scanning electron microscopy the presence of such interstices in a syntactic foam composition prepared in accordance with the methods of the present invention.

The pharmaceutical could also be active or inactive metabolites of active pharmaceutical ingredients or salts of the metabolites of active pharmaceutical ingredients.

The pharmaceutical could also be a pro-drug which after oral administration generates active or inactive metabolites.

The pharmaceutical could also be a precursor which after oral administration generates active or inactive metabolites.

The pharmaceutical could also be prepared so as to become systemically available over a period of not less than two hours after administration to a human or other mammal.

The pharmaceutical or pharmaceutical active could also be a time-released or controlled release preparation such that the pharmaceutical elicits pharmacological or therapeutic activity after ingestion of the pharmaceutical preparation comprising the syntactic foam carrier and the medicine.

EXAMPLES

The invention is illustrated by way of some Examples. The following examples are provided as specific embodiments of the present invention, and should be taken as illustrative and not as limiting the scope of the invention in any way.

In the following, Examples 1 to 6 inclusive are directed towards exemplifying the methodology for the preparation of one or more syntactic foams of the present invention. The remaining examples, 7 to 12, are directed towards exemplifying the preparation and use of one or more syntactic foams of the present invention as carriers for medicines.

Example 1

Carbopol® 971P NF (B.F. Goodrich Co) (100 gm), hydroxyethyl cellulose (Dow Chemicals) (100 gm), Cellulose microspheres (FMC Corporation) (150 gm) and Silicic anhidride (LV Lomas,) (20 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying.

Example 2

Carbopolt® 974P NF (B.F. Goodrich Co) (80 gm), hydroxyethyl cellulose (Dow Chemicals) (100 gm), Cellulose microspheres (FMC Corporation) (150 gm) and Silicic anhidride (LV Lomas,) (20 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying.

Example 3

Carbopol® 971P NF (B.F. Goodrich Co) (60 gm), Carbopol® 974P NF (B.F. Goodrich Co) (40 gm), hydroxyethyl cellulose (Dow Chemicals) (100 gm), Cellulose microspheres (FMC Corporation) (150 gm) and Silicic anhidride (LV Lomas,) (20 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying.

Example 4

Carbopol® 971P NF (B.F. Goodrich Co) (100 gm), hydroxyethyl cellulose (Dow Chemicals) (150 gm), Cellulose microspheres (FMC Corporation) (100 gm), Mannitol (50 gm) and Silicic anhidride (LV Lomas,) (10 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying.

Example 5

Carbopol® 971P NF (B.F. Goodrich Co) (100 gm), hydroxypropyl Methyl cellulose (Dow Chemicals) (150 gm), Cellulose microspheres (FMC Corporation) (100 gm), Mannitol (50 gm) and Silicic anhidride (LV Lomas) (10 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying.

Example 6

Carbopol® 971P NF (B.F. Goodrich Co) (100 gm), polyethelene oxide (Union Carbide) (150 gm), Cellulose microspheres (FMC Corporation) (100 gm), Mannitol (50 gm) and Silicic anhidride (LV Lomas) (10 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying.

Example 7

Metoprolol succinate (550 gm) was added to the admixture from example 1 and subjected to high shear agitation for 2 minutes before reacting with 2-propanol as was described in example 1. A stable syntactic deformable and compressible dendritic solid foam which could be shaped before drying was obtained. This was dried at 40 degrees centigrade until a loss of drying of 1.5 was obtained. The dried foam disentangled by size reduction to obtain discrete particles. The free flowing particles was reassembled and shaped by compression in a mold. The shaped units when subjected to an aqueous medium released metropolol over a period of not less than 3 hours.

Example 8

Metoprolol succinate was replaced by Pseudoephedrine sulphate (625 mg). The shaped units when subjected to an aqueous medium released Pseudoephedrine over a period of not less than 3 hours.

Example 9

Metoprolol succinate was replaced by Acetominophen and the admixture from example 5 was used. The shaped units when subjected to an aqueous medium released Acetominophen over a period of not less than 3 hours.

Example 10

L-arginine hydrochloride (625 gm) was added to the admixture from example 5 and subjected to high shear agitation for 2 minutes before reacting with 2-propanol as was described in example 5. A stable syntactic deformable and compressible dendritic solid foam which could be shaped before drying was obtained. This was dried at 40 degrees centigrade until a loss on drying of 1.5 was obtained. The dried foam was disentangled by size reduction to obtain discrete particles. The free flowing particles were re-assembled and shaped by compression in a caplet mold. The shaped units where coated with an enteric coat of cellulose acetate phthalate and when subjected to an aqueous medium released larginine over a period of not less than 3 hours. A syntactic foam in the shape of a caplet was created and which could be used for the delivery of a medicine Example 11

Microspheres of Levodopa consisting of Levodopa: Avicel PH101: Hydroxyethyl cellulose in a ratio of 25:70:5 was made by extrusion spheronization technique. The microspheres (750 gm), Carbopol® 971P NF (B.F. Goodrich Co) (150 gm), hydroxypropyl Methyl cellulose (Dow Chemicals) (50 gm), Sorbitol (50 gm) and Silicic anhidride (LV Lomas) (10 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying. This was dried at 40 degrees centigrade until a loss of drying of <2.0 was obtained. The dried foam was disentangled by size reduction to obtain discrete particles. The free flowing particles were reassembled and shaped by compression in a tablet shaped mold. A syntactic foam in the shape of a tablet was created which comprised Levodopa and could be used for the delivery of this medicinal product. It was further noted that when the shaped units were subjected to an aqueous medium, Levodopa was released over a period of time of not less than three hours.

Example 12

The microspheres were made by coating nonpareil sugar seeds with drug (divalproex sodium) laden Eudragit L100 solution. The microspheres (725 gm), Carbopol® 971P NF (B.F. Goodrich Co) (100 gm), polyethylene oxide (Union carbide) (100 gm), Mannitol (50 gm) and Silicic anhidride (LV Lomas) (10 gm) was added together and admixed in a high shear mixer at 1500 rpm for 3 minutes (Robot Cop). The resulting admixture was reacted with 130 ml of 2-propanol at 20 degrees centigrade while simultaneously subjecting the admixture to high shear forces (1500 rpm) in the high shear mixer. Reaction time and high shear agitation was for 45 seconds. This mixing created a uniform stable syntactic deformable and compressible dendritic solid foam which could be shaped before drying. This was dried at 40 degrees centigrade until a loss of drying of <2.0 was obtained. The dried foam was disentangled by size reduction to obtain discrete particles. The free flowing particles was reassembled and shaped by compression in a mold. The shaped units when subjected to an aqueous medium released divalproex over a period of not less than 3 hours.

Other embodiments, modifications, variations and equivalents of the present invention will be appreciated by a person skilled in the art as falling within the scope of the appended claims.

What is claimed is:

1. A method of preparing a deformable syntactic foam for the delivery of a compound or chemical, the method comprising:
    a) mixing together one or more homopolymer resins, one or more binders, and one or more stabilizers to form a blended mixture having a LOD of from about 1% to about 10%; and
    b) mixing said blended mixture with one or more organic solvents under conditions of high shear at temperatures of from about 10° C. to about 25° C. until a foam composition is formed wherein said foam composition is deformable.

2. The method according to claim 1 wherein said mixture in step (a) further comprises a particulate substance.

3. The method according to claim 2 wherein said particulate substance is substantially spherical.

4. The method according to claim 3 wherein said particulate substance is a plurality of microspheres.

5. The method according to claim 4 wherein during the mixing in step a) the LOD is checked intermittently until the LOD of the mixture is from about 2 percent to about 25 percent.

6. The method according to claim 5 comprising a further step of separating said syntactic foam into particles.

7. The method according to claim 6 wherein said syntactic foam is lyophilized or freeze dried before separating said syntactic foam into particles.

8. The method according to claim 7 wherein said further step of separating comprises milling the foam.

9. The method according to claim 8 wherein said step of separating further comprises a drying step at from about 25° C. to about 60° C.

10. The method according to claim 9 wherein the approximate diameter of said particles is about 1000 $\mu$m.

11. The method according to claim 9 wherein the approximate diameter of said particles is less than about 1000 $\mu$m.

12. The method according to claim 7 wherein said step of separating is preceded by a step of treating said syntactic foam to make it rigid.

13. The method according to claim 12 wherein said step of treating said syntactic foam to make rigid comprises contacting said syntactic foam with a cryogenic fluid.

14. The method according to claim 13 wherein said cryogenic fluid is selected from the group consisting of liquid nitrogen and liquid carbon dioxide.

15. The method according to claim 14, wherein the approximate diameter of said particles is about 100 µm.

16. The method according to claim 14 wherein the approximate diameter of said particles is less than about 1000 µm.

17. The method according to claim 6 wherein the particles are subsequently molded into a shaped composite.

18. The method according to claim 17 wherein the shape of the shaped composite is selected from the group of shapes consisting of round, triangular, rectangular, polygonal, cylindrical, oval, oblong, capsule, tablet and caplet.

19. The method according to claim 18 wherein said stabilizer is silicic anhydride.

20. The method according to claim 19 wherein said organic solvent is 2-propanol.

21. The method according to claim 20 wherein the homopolymer resin is a carboxyvinyl polymer.

22. The method according to claim 21 wherein the microspheres are selected from the group consisting of silica, sucrose, glucose, lactose, dextrose, sorbitol, mannitol, xylitol, dextrates, poly(lactic acid), poly(glycolic acid), poly(glycolic acid-co-lactic acid), poly($\epsilon$-caprolactone), poly(malic acid), cellulose, microcrystalline cellulose, metal, glass and small beads.

23. The method according to claim 22 wherein the microspheres are cellulose microspheres.

24. The method according to claim 23 wherein the blended mixture further comprises a binder.

25. The method according to claim 24 wherein the binder is selected from the group consisting of high molecular weight polysaccharide, xanthan gum, d-α-tocopherol polyethylene glycol 1000 succinate, starch NF, povidone, copolyvidone NF, polyvinyl alcohols, glyceryl behenate, polyethelene glycols, polyethelene oxides, cellulose binders, hydroxypropyl Methylcaellulose USP and hydroxyethyl Cellulose NF.

26. The method according to claim 25 wherein the binder is a high molecular weight polysaccharide.

27. The method according to claim 25 wherein the high molecular weight polysaccharide is Xanthan gum.

28. The method according to claim 25 wherein the binder is d-α-tocopherol polyethylene glycol 1000 succinate.

29. A method of manufacturing a pharmaceutical carrier, the method comprising the steps of:
   a) mixing together:
      i) one or more pharmaceutically acceptable homopolymer resins;
      ii) one or more pharmaceutically acceptable binders;
      iii) pharmaceutically acceptable microspheres, and
      iv) one or more pharmaceutically acceptable stabilizers to form a blended mixture having an LOD of from about 1% to about 10%;
   b) mixing said blended mixture with one or more pharmaceutically acceptable organic solvents under conditions of high shear at temperatures of from about 10° C. to about 25° C. until a foam composition is formed wherein said foam composition is deformable; and
   c) reducing the size of the deformable syntactic foam to permit reassembly into a shaped composite.

30. The method according to claim 29 wherein said deformable syntactic foam is reduced in size by drying (LOD less than about 5%) and then milling.

31. The method according to claim 30 wherein said stabilizer is silicic anhydride.

32. The method according to claim 31 wherein said organic solvent is 2-propanol.

33. The method according to claim 32 wherein the homopolymer resin is a carboxyvinyl polymer.

34. The method according to claim 33 wherein the microspheres are selected from the group consisting of silica, sucrose, glucose, lactose, dextrose, sorbitol, mannitol, xylitol, dextrates, poly(lactic acid), poly(glycolic acid), poly(glycolic acid-co-lactic acid), poly($\epsilon$-caprolactone), poly(malic acid), cellulose, microcrystalline cellulose, metal, glass and-small beads.

35. The method according to claim 34 wherein the microspheres are cellulose microspheres.

36. The method according to claim 35 wherein the blended mixture further comprises a binder.

37. The method according to claim 36 wherein the binder is selected from the group consisting of high molecular weight polysaccharide, xanthan gum, d-α-tocopherol polyethylene glycol 1000 succinate, starch NF, povidone, copolyvidone NF, polyvinyl alcohols, glyceryl behenate, polyethelene glycols, polyethelene oxides, cellulose binders, hydroxypropyl Methylcellulose USP and hydroxyethyl Cellulose NF.

38. The method according to claim 37 wherein the binder is a high molecular weight polysaccharide.

39. The method according to claim 37 wherein the binder is Xanthan gum.

40. The method according to claim 37 wherein the binder is d-α-tocopherol polyethylene glycol 1000 succinate.

41. A pharmaceutical composition comprising a pharmaceutical and a pharmaceutical carrier wherein said pharmaceutical carrier is prepared in accordance with the method of claim 29.

42. The composition according to claim 41 wherein the pharmaceutical is selected from the group consisting of human and veterinary medicines.

43. The composition according to claim 42 wherein the pharmaceutical active is selected from the group of pharmaceuticals having one or more active ingredients selected from the group consisting of Acarbose, Acetaminophen/Codeine, Albuterol, Alendronate, Allopurinol, Alprazolam, Amitriptyline, Amlodipine, Amlodipine/Benazepril, Amoxicillin, Amoxicillin/Clavulanate, Amphetamine Mixed Salts, Aspirin, Atenolol, Atorvastatin, Azithrorycin, Beclomethasone, Benazepril, Bisoprolol/HCTZ, Brimonidine, Carbidopa-Levodopa, Calcitonin, Carisoprodol, Carvedilol, Cefprozil, Cefuroxime, Celecoxib, Cephalexin, Cetirizine, Ciprofloxacin, Cisapride, Citalopram, Clarithromycin, Clonazepam, Clonidine, Clopidogrel, Clotrimazole/Betamethasone, Cyclobenzaprine, d-phenylalanine amino acid derivative, Diazepam, Misoprostol, Digoxin, Divalproex, Donepezil, Doxazosin, Enalapril, Erthromycin, Estradiol, Ethinyl Estradiol/Norethindrone, Famotidine, Felopidine, Fexofenadine, Fexofenadine/Pseudoephedrine, Fluoxetine, Fluticasone Propionate, Fluvastatin, Fluvoxamine, Fosinopril, Furosemide, Gemfibrozil, Glimepiride, Glyburide, Granisetron, Guaifenesin/Phenylpropanolamine, Hydrochlorothiazine, Hydrocodone w/APAP, Ibuprofen, Ipratropium, Ipratropium/Albuterol, Irbesartan, Isosorbide Mononitrate, Lansoprazole, Latanoprost, Levofloxacin, Levonorgestrel/Ethinyl Estradiol, Levothyroxine, Lisinopril, Lisinopril/HCTZ, Loratadine, Loratidine/Pseudoephedrine, Lorazepam, Losartan, Losartan/HCTZ, Lovastatin, Mateglinide, Mesalamine, Methylprednisolone, Metoprolol, Miglitol, Mometasone, Montelukast, Morphine, Mupirocin, Naproxen, Nisoldipine, Nitrofurantoin, Nizatidine, Ofloxacin, Olanzapine, Ondansetron, Oxaprozin, Oxycodone, Oxycodone/APAP, Paroxetine, Penicillin VK, Phenytoin, Potassium Chloride, Pramipexole, Pravastatin, Prednisone, Promethazine, Propoxyphene N/APAP, Propranolol, Quetiapine, Quinapril, Raloxitene, Ramipril, Ranitidine, Repaglinide, Risperidone, Rofecoxib, Salmeterol, Sertraline, Sildenafil, Simvastatin, Sotalol, Sumatriptan, Tamoxifen, Tamsulosin, Temazepam, Terazoain, Terbinafine, Tobramycin/Dexamethasone, Tolterodine, Tranylcypromine, Trazodone, Triamterine/HCTZ, Troglitazone, Valsartan, Venlafaxine, Warfaxin, Zafirlukast, and Zolpidem.

44. The composition according to claim 42 wherein said pharmaceutical active is selected from the group consisting of abacavir, amprenavir, staviudine, zalcitabine, didanosine, delavivdine, efavirenz, hydroxyurea, indinavir, lamivudine, lopinavir, nelfinavir, nevirapine, ritonavir, saquinavir and zidovudine.

45. The composition according to claim 42 wherein said pharmaceutical active is a cyclooxygenase inhibitor.

46. The composition according to claim 45 wherein the cyclooxygenase inhibitor is COX-2.

47. The composition according to claim 46 wherein the COX-2 cyclooxygenase inhibitor is celecoxib or rofecoxib.

48. The composition according to claim 41 comprising a further step of applying a coating agent to the foam before the size reduction step (c).

49. The composition according to claim 41 wherein the size reduced foam is molded into a shaped composite.

50. The composition according to claim 49 wherein a coating agent is applied to the size reduced foam after it is molded into a shaped composite.

51. The composition according to claim 50 wherein the shape of the shaped composite is selected from the group of shapes consisting of round, triangular, rectangular, polygonal, cylindrical, oval, oblong, capsule, tablet and caplet.

52. The composition according to claim 41 wherein the pharmaceutical or pharmaceutical active is in interstices between said microspheres.

53. The composition according to claim 41 wherein the pharmaceutical or pharmaceutical active is non-covalently bound to said microspheres.

54. The composition according to claim 41 wherein the pharmaceutical or pharmaceutical active is covalently bound to said microspheres.

55. The composition according to claim 41 wherein the pharmaceutical or pharmaceutical active is contained within said microspheres.

56. The composition according to claim 41 wherein the pharmaceutical is active or inactive metabolites of active pharmaceutical ingredients or salts of the metabolites of active pharmaceutical ingredients.

57. The composition according to claim 41 wherein the pharmaceutical is a pro-drug which after oral administration generates active or inactive metabolites.

58. The composition according to claim 41 wherein the pharmaceutical is as a precursor which after oral administration generates active or inactive metabolites.

59. The composition according to claim 41 wherein the said pharmaceutical is prepared so as to become systemically available over a period of not less than two hours after administration to a human or other mammal.

60. The composition according to claim 41 wherein said pharmaceutical composition is a time-release preparation.

61. The composition according to claim 60 wherein said pharmaceutical elicits pharmacological or therapeutic activity.

62. A method of preparing a deformable syntactic foam for the delivery of a compound or chemical, the method comprising:
 a) mixing together a carboxyvinyl polymer, a high molecular weight polysaccharide, silicic anhydride and a suitable microsphere to form a blended mixture having a LOD of from about 1% to about 10%; and
 b) mixing the mixture of a) with an organic solvent under conditions of high shear at temperatures of from about 10° C. to about 25° C. until a foam composition is formed wherein said foam composition is deformable and has a LOD of about 8% to about 20%.

* * * * *